US008717852B2

(12) United States Patent
Cohen et al.

(10) Patent No.: US 8,717,852 B2
(45) Date of Patent: May 6, 2014

(54) APPARATUS FOR PROVIDING CONDITION-BASED VIBROTACTILE FEEDBACK

(71) Applicant: Immersion Corporation, San Jose, CA (US)

(72) Inventors: Robert F. Cohen, Kensington, MD (US); Walter E. Ratzat, Silver Spring, MD (US); Tianning Xu, Duluth, GA (US)

(73) Assignee: Immersion Corporation, San Jose, CA (US)

( * ) Notice: Subject to any disclaimer, the term of this patent is extended or adjusted under 35 U.S.C. 154(b) by 0 days.

(21) Appl. No.: 13/734,988

(22) Filed: Jan. 6, 2013

(65) Prior Publication Data
US 2013/0120153 A1 May 16, 2013

Related U.S. Application Data

(62) Division of application No. 12/435,323, filed on May 4, 2009, now Pat. No. 8,351,299.

(60) Provisional application No. 61/049,806, filed on May 2, 2008.

(51) Int. Cl.
G04B 47/00 (2006.01)
G04F 10/00 (2006.01)
A46B 15/00 (2006.01)
A61M 16/00 (2006.01)

(52) U.S. Cl.
USPC .............. 368/10; 368/109; 15/105; 15/167.1; 324/207.15; 340/686.1

(58) Field of Classification Search
USPC .......... 368/10, 107–109; 15/22.1, 105, 167.1; 324/207.15, 207.16; 340/686.1
See application file for complete search history.

(56) References Cited

U.S. PATENT DOCUMENTS

| 3,235,790 | A | * | 2/1966 | Collins | 323/347 |
| 4,253,212 | A | * | 3/1981 | Fujita | 15/167.1 |
| 4,337,402 | A | * | 6/1982 | Nowakowski | 307/121 |
| 4,571,680 | A | * | 2/1986 | Wu | 377/24.2 |
| 4,716,614 | A | * | 1/1988 | Jones et al. | 15/105 |
| 5,361,241 | A | * | 11/1994 | Ferrara et al. | 368/281 |
| 5,438,726 | A | * | 8/1995 | Leite | 15/105 |
| 5,485,646 | A | * | 1/1996 | Merritt | 15/105 |
| 5,544,382 | A | * | 8/1996 | Giuliani et al. | 15/22.1 |
| 5,581,519 | A | * | 12/1996 | Hara et al. | 368/64 |

(Continued)

FOREIGN PATENT DOCUMENTS

| AU | 637709 | 6/1993 |
| GB | 2191863 | 12/1987 |

(Continued)

*Primary Examiner* — Vit W Miska
(74) *Attorney, Agent, or Firm* — Medler Ferro PLLC

(57) ABSTRACT

Systems and methods for monitoring motion parameters of an object are described in the present disclosure. In an embodiment, a sensor, coupled to a housing, senses motion associated with the housing and provides a sensor output based on the sensed motion. A processing device receives the sensor output, accumulates counts associated with the sensor output, and provides an output once a threshold associated with the accumulated counts is reached. A vibrotactile device, that receives the output from the processing device, provides a haptic output in response to the output from the processing device.

4 Claims, 5 Drawing Sheets

(56) References Cited

U.S. PATENT DOCUMENTS

| | | | |
|---|---|---|---|
| 5,699,322 A * | 12/1997 | Born | 368/66 |
| 5,784,742 A * | 7/1998 | Giuliani et al. | 15/22.1 |
| 5,894,453 A * | 4/1999 | Pond | 368/10 |
| 5,924,159 A * | 7/1999 | Haitin | 15/105 |
| 6,029,303 A * | 2/2000 | Dewan | 15/105 |
| 6,106,294 A * | 8/2000 | Daniel | 433/216 |
| 6,147,936 A * | 11/2000 | Nakajima | 368/205 |
| 6,389,633 B1 * | 5/2002 | Rosen | 15/105 |
| 6,536,068 B1 * | 3/2003 | Yang et al. | 15/105 |
| 6,796,925 B2 * | 9/2004 | Martinez et al. | 482/8 |
| 7,354,383 B2 * | 4/2008 | Bardha | 482/82 |
| 7,876,070 B2 * | 1/2011 | Kitahara | 320/134 |
| 2002/0183959 A1 * | 12/2002 | Savill et al. | 702/150 |
| 2003/0062041 A1 * | 4/2003 | Keith et al. | 128/203.12 |
| 2003/0063011 A1 | 4/2003 | Rosen | |
| 2003/0171189 A1 * | 9/2003 | Kaufman | 482/8 |
| 2003/0192547 A1 * | 10/2003 | Lurie et al. | 128/207.12 |
| 2004/0134000 A1 * | 7/2004 | Hilfinger et al. | 15/22.1 |
| 2008/0060148 A1 * | 3/2008 | Pinyayev et al. | 15/22.1 |
| 2008/0109973 A1 * | 5/2008 | Farrell et al. | 15/4 |
| 2009/0064430 A1 * | 3/2009 | Jimenez et al. | 15/22.1 |
| 2009/0092955 A1 * | 4/2009 | Hwang | 434/263 |
| 2010/0106336 A1 * | 4/2010 | Hwang et al. | 700/280 |

FOREIGN PATENT DOCUMENTS

| | | |
|---|---|---|
| GB | 2424084 | 9/2006 |
| WO | WO-01/70092 | 9/2001 |
| WO | WO-2006/137648 | 12/2006 |
| WO | WO 2008/072871 * | 6/2008 |

* cited by examiner

APPARATUS FOR PROVIDING CONDITION-BASED VIBROTACTILE FEEDBACK

CROSS-REFERENCE TO RELATED APPLICATIONS

The present application is a divisional of U.S. application Ser. No. 12/435,323, filed on May 4, 2009, and now U.S. Pat. No. 8,351,299, which claims the benefit of U.S. Appl. No. 61/049,806, filed on May 2, 2008, and entitled "Toothbrush with Brush Stroke Monitoring System," each of which is incorporated by reference herein in its entirety.

TECHNICAL FIELD

The present disclosure generally relates to sensing conditions and providing alerts in response to those sensed conditions and more particularly to sensing time-based conditions and in some applications, providing vibrotactile feedback in response thereto.

BACKGROUND OF THE INVENTION

There are many benefits to practicing proper dental hygiene. By brushing one's teeth, flossing, and using antiseptic mouthwash, a person can help prevent tooth decay, maintain fresh breath, and reduce unpleasant visits with an endodontist or oral surgeon. It is recommended that people brush their teeth twice a day for about two minutes each session. Other recommendations include making regular visits to the dentist and periodically replacing old toothbrushes. However, because of various reasons, people do not always follow these guidelines for proper dental hygiene and might experience problems as a result.

Over the years, toothbrush manufacturers have made many changes in the designs of toothbrushes. Generally, the design of a toothbrush does not greatly impact the quality of the dental care offered to a user. Thus, the choice of toothbrushes is mainly a matter of personal preference. Electric toothbrushes provide an additional choice in the selection of dental care. One advantage of electric toothbrushes is that they provide the needed movement of the brushing bristles and they do the work for the user in this regard. Some drawbacks with respect to electric toothbrushes can be the higher cost versus regular toothbrushes and the added responsibility of maintaining fresh batteries to power the device although rechargeable options do exist.

The various designs and features of toothbrushes not only provide a marketing opportunity for the manufacturers, but also the toothbrush features may be used as a motivation for people to take better care of their teeth. Additionally, since it can be particularly challenging at times to teach and motivate children to practice adequate dental hygiene, toothbrush manufacturers sometimes add an element of entertainment in the teeth brushing routine.

With particular reference to the guideline that a person should brush for a time of two minutes, timers can be used to alert the user when the time has expired. However, depending on the speed that people brush their teeth, two minutes might not be long enough to adequately brush the entire mouth or it might be more than enough time. Some of the more expensive electric toothbrushes have been designed with a built-in timer and an alarm for indicating when a predetermined time expires. The higher cost of these electric toothbrushes can discourage some people from purchasing these types.

Further, conventional alarms for such toothbrushes, and other devices, generally, may not be sufficient to effectively alert the users of these devices, when motion, or other condition, is sensed. Users of such devices may not perceive the alarm particularly when operating in hectic environments, (e.g., bathrooms on weekday mornings, emergency rooms, etc.), and/or when bombarded with competing audio and/or visual stimuli.

SUMMARY OF THE INVENTION

The present disclosure describes systems and methods for monitoring motion parameters of an object manipulated by a user. In some embodiments, for example, the object to be monitored is a toothbrush comprising a handle and bristles, where the bristles have first ends that are supported at one end of the handle. The toothbrush also includes a monitoring mechanism incorporated in the handle. The monitoring mechanism monitors a plurality of brush strokes that a user executes with the toothbrush.

The present disclosure describes apparatus and methods for providing feedback in response to a sensed condition. In some embodiments, the sensed condition is one or more motion parameters. In some embodiments, the sensed condition is time. In some embodiments, the feedback is vibrotactile feedback. In some embodiments, the apparatus includes a condition sensor that provides an output in response to the sensed condition and a vibrotactile device that receives the output and provides a haptic output in response to the received output from the condition sensor.

The present disclosure describes apparatus and method for providing vibrotactile feedback in response to expiration of at least one time period. In some embodiments, an apparatus includes a housing. The apparatus also includes a timer coupled to the housing that measures at least one time period and provides a timer output on expiration of the at least one time period. The apparatus also includes a vibrotactile device that receives the timer output and provides a haptic output in response to the received timer output.

Other features, advantages, and implementations of the present disclosure, not expressly disclosed herein, will be apparent to one of ordinary skill in the art upon examination of the following detailed description and accompanying drawings. It is intended that such implied implementations of the present disclosure be included herein.

BRIEF DESCRIPTION OF THE DRAWINGS

The components of the following figures are illustrated to emphasize the general principles of the present disclosure and are not necessarily drawn to scale. Reference characters designating corresponding components are repeated as necessary throughout the figures for the sake of consistency and clarity.

DETAILED DESCRIPTION

Conventional tooth brushing guidelines recommend that people brush their teeth for two minutes each time they brush. However, since brushing techniques can differ from person to person, two minutes may not be long enough for some people while two minutes may be more than enough. The present disclosure describes systems and methods for monitoring motion characteristics of a toothbrush during use. Any parameter or combination of parameters associated with motion, such as vibration, oscillation, rotation, acceleration, force, velocity, change of direction, etc., can be sensed. By summing each motion component, a total accumulation of motions can be determined to monitor the amount of motion that the user exerts on the toothbrush while brushing. The systems and methods of the present disclosure can then determine when the amount of brushing has reached a predetermined threshold. This threshold can be established based on brushing time guidelines in addition to an average brushing speed. However, since brushing speed may differ from one user to another, the user of the toothbrush as described in the present disclosure is given an indication when an adequate brushing threshold has been reached, which is based on motion of the toothbrush and not necessarily based on time.

The examples described in the present disclosure relate to toothbrushes and measuring brush strokes. However, it should be understood that the teachings of the present disclosure might also encompass other devices or tools that are used in a repetitive manner for a certain duration. Instead of simply measuring time to determine if a task has been completed adequately, the present disclosure describes systems and methods for measuring vibrations, oscillations, strokes, or forces related to these motions that a user exerts on the device or tool. In addition to toothbrushes, the systems and methods described herein may also apply to other suitable devices, tools, or instruments—such as, for example, painting, staining, or polishing devices; scrubbing, washing, cleaning, or waxing devices; massage therapy devices; mixing devices; etc. Other advantages will become apparent to one of ordinary skill in the art from an understanding of the present disclosure.

Figure 1:
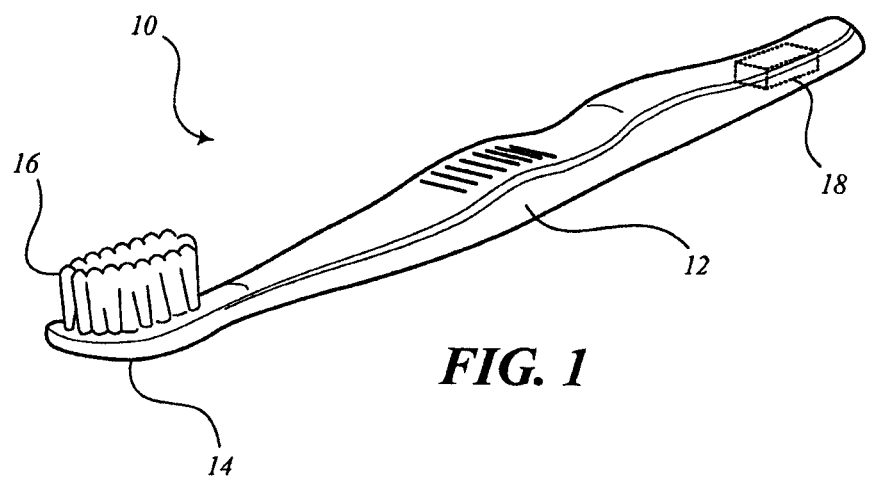
FIG. 1 is an illustration of a toothbrush having a brush stroke monitoring system according to one embodiment.

FIG. 1 illustrates a view of an embodiment of a toothbrush 10. In this implementation, toothbrush 10 includes a handle 12, head 14, bristles 16, and a brush stroke monitoring system 18. Handle 12 and head 14 may form one unitary body that supports first ends of bristles 16 in head 14 such that the other ends of bristles 16 are oriented away from head 14. Handle 12, head 14, and bristles 16 may include any suitable form or design and may even include forms or designs similar to conventional toothbrushes. In contrast to conventional toothbrushes, however, toothbrush 10 of the present disclosure further includes brush stroke monitoring system 18, which can be at least partially positioned within handle 12, such as at one end of handle 12 as is shown in FIG. 1.

Brush stroke monitoring system 18 is configured to detect motion of toothbrush 10. When a user provides a motion, such as vibration or oscillation forces, to toothbrush 10 in a normal brushing motion, brush stroke monitoring system 18 detects this motion. Brush stroke monitoring system 18 may be configured to detect changes in force, acceleration, or other parameter caused by a directional change of toothbrush 10. To monitor motion, brush stroke monitoring system 18 may include any suitable detection device. In some embodiments, brush stroke monitoring system 18 may monitor motion along more than one axis. Brush stroke monitoring system 18 may also monitor rotational motion about one or more axes. Although not shown specifically in FIG. 1, brush stroke monitoring system 18 may include a device for indicating to the user when the total amount of brushing motions is sufficient.

Figure 2:
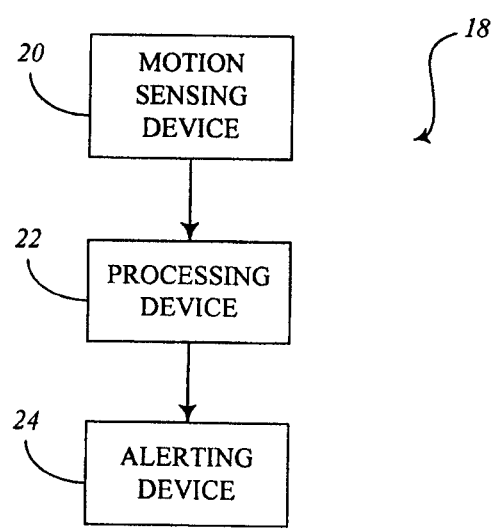
FIG. 2 is a block diagram of the brush stroke monitoring system shown in FIG. 1 according to one embodiment.

FIG. 2 is a block diagram illustrating an embodiment of the brush stroke monitoring system 18 shown in FIG. 1. Regarding embodiments in which brush stroke monitoring system 18 is supported on a device, tool, or instrument other than toothbrush 10, as suggested above, brush stroke monitoring system 18 can be configured to measure any suitable parameter related to motion of the particular device. Other modifications can be made, as would be understood by one of ordinary skill in the art, to measure and analyze different aspects of motions based on the type of device being manipulated and how it is intended to be manipulated. When a device is moved in a predictable and repetitive manner, an accumulation of each measured motion parameter is calculated to determine when a threshold is reached. Depending on the particular device and application, the threshold value may be set as needed for allowing an optimum or recommended motion of the device.

In the embodiment shown in FIG. 2, brush stroke monitoring system 18 includes a motion sensing device 20, a processing device 22, and an alerting device 24. Motion sensing device 20 detects motion of toothbrush 10 caused by the user manipulating toothbrush 10, and more particularly may detect motion only in a regular brushing pattern, e.g. moving head 14 side to side. In some embodiments, processing device 22 can be configured to detect the completion of a single stroke (e.g. from up to down) or an entire stroke cycle (e.g., from up to down and back to up). When used in this manner, processing device 22 is associated with or includes a counter that is configured to count the number of strokes or stroke cycles to determine when a predetermined threshold is reached. For example, if a threshold is set at 500 strokes, then processing device 22 determines when toothbrush 10 has been manipulated in a way to brush the user's teeth for 500 strokes.

In other embodiments, processing device 22 may be configured to detect the force of the strokes or even the length or distance of the strokes, depending on the application. By analyzing the physics of the motion, calculations can be made to determine the manner in which strokes of toothbrush 10 are exerted. Stroke force or stroke length can be calculated for each individual stroke, and then using a summing device, which can be included in or associated with processing device 22, processing device 22 can sum the values to obtain an accumulated total. Threshold values can be set for a total stroke force or total stroke length as necessary. When the accumulative total reaches a predetermined threshold, processing device 22 determines that the user has brushed for an adequate amount. It should be noted that the thresholds associated with these embodiments are not evaluated with units of time, i.e., seconds or minutes, but rather are evaluated with units related to a count number or an accumulative total amount.

When it is determined that the threshold is reached, processing device 22 instructs alerting device 24 to send an alert to the user indicating that the threshold has been reached. The user may then discontinue the motion activity, i.e., brushing. Alerting device 24 may include any suitable combination of sensory outputs for stimulating one or more of the user's senses. For example, alerting device 24 may include a visual indicator, such as a light emitting diode (LED) or other illumination device. Alerting device 24 may include an audible indicator, such as a buzzer or other audio device. In other embodiments, alerting device 24 may include a vibrotactile device for providing a temporary haptic output. In still other embodiments, alerting device 24 may include a device for releasing a distinct scent that the user can smell or a distinct taste that can be applied to the bristles.

Brush stroke monitoring system 18 may further include one or more input devices allowing the user to input commands. For example, the input devices may include a button, switch, or other entry device that instructs processing device 22 to reset all counters or accumulating storage devices to zero. When reset, brush stroke monitoring system 18 can begin a new session, e.g., a new teeth brushing session. Input devices may further include an on/off switch. In other embodiments, processing device 22 may detect when toothbrush 10 is inactive for a certain length of time. When inactive, processing device 22 may turn power off, for embodiments requiring power, and/or may reset all summing devices to zero.

In some embodiments, processing device 22 may be associated with memory that is configured to store information, data, instructions, and/or software code. The memory may include any combination of volatile memory, such as random access memory (RAM), dynamic RAM (DRAM), etc., and/or non-volatile memory, such as read only memory (ROM), electrically erasable programmable ROM (EEPROM), flash memory, etc.

Memory can also be configured to store program code that enables processing device 22 to execute procedures to analyze and process the motion parameters. Various logical instructions or commands may be included in program code for processing motion parameters. The motion parameter processing program of the present disclosure can be implemented in hardware, software, firmware, or a combination thereof. When implemented in software or firmware, the motion parameter processing program can be stored in memory and executed by processing device 22. When implemented in hardware, the motion parameter processing program can be implemented in processing device 22 using discrete logic circuitry, an application specific integrated circuit (ASIC), a programmable gate array (PGA), a field programmable gate array (FPGA), etc., or any combination thereof.

Specific embodiments of motion sensing device 20 are described here. In a first embodiment, motion sensing device 20 may be configured as an accelerometer. The accelerometer detects the changes in velocity caused by forces acting on the device being monitored. The detected forces (and/or accelerations) can be used in an accumulative manner to sum the total forces that have been applied. In other embodiments, the accelerometer may simply detect when the direction of the motion changes signs, indicating a change in direction of the monitored device. A detected change of direction is further indicative of the end of one stroke and the beginning of another. When used in this way, processing device 22 may include a counter for counting the number of direction changes, i.e., strokes. From one direction change to the next direction change can be considered, for example, as one stroke or half of a stroke cycle.

Regarding a second embodiment, motion sensing device 20 may be configured as a combination of at least one magnetic element and at least one electrical element. For example, the combination may include a stationary electrical coil surrounding a magnetic rod that is allowed to move along the axis formed by the coil. In this embodiment, movement of the device causes the moveable magnetic rod to move in a direction within the coil that results in an electrical current flowing through the coil. When the device is moved in the opposite direction, the magnetic rod moves within the coil in the opposite direction resulting in a current flow through the coil in the opposite direction. To allow the total current produced in this way to be monitored, motion sensing device 20 may further include a full-wave rectifier for providing only the magnitude of the currents without the positive or negative signs.

Processing device 22 in this particular embodiment may include at least a capacitor that is charged up by the current flow. Processing device 22 may further include a charge sensing device for detecting when the capacitor has reached a certain threshold. When the threshold is reached, capacitor is discharged through alerting device 24. It should be noted that this embodiment does not require the use of a power source since the capacitor is charged up using current generated by the user's motion.

In yet another embodiment of motion sensing device 20, a "ball in a cage" configuration can be used. In this implementation, a miniature ball is formed inside a miniature cage having contacts for detecting where the ball is located within the cage. When motion of the device causes the ball to roll or bounce to another side of the cage, the respective contacts detect its position. From these detections, the forces acting on the ball in the cage can be computed. With the forces computed, processing device 22 can sum the forces to determine when a total threshold is reached. According to other embodiments, processing device 22 may include a counter to count the number of direction changes, which is therefore indicative of the number of strokes or vibrations. In other implementations, processing device 22 uses a capacitor that is charged up in response to the detected force to determine an accumulative total force.

Motion sensing device 20, according to other embodiments, may be configured as a force sensor for sensing the force of toothbrush strokes. In this regard, the force sensor can include a piezoelectric element. At the same time, the piezoelectric element may also be configured to include an electrical generator for providing power to processing device 22, so as to both sense force and generate power. In some embodiments, the force sensor may receive force directly or indirectly from bristles 16 when they are in contact with the user's teeth. The force sensor may therefore be configured to sense force on bristles 16 in a number of directions, e.g. longitudinal (compression) force, lateral force, or other possible forces. With respect to these embodiments in which motion sensing device 20 includes a force sensor, processing device 22 may be configured to sense an accumulative force that has been applied to the teeth during the brushing session and alert the user when the total force reaches a predetermined threshold value.

Figure 3:
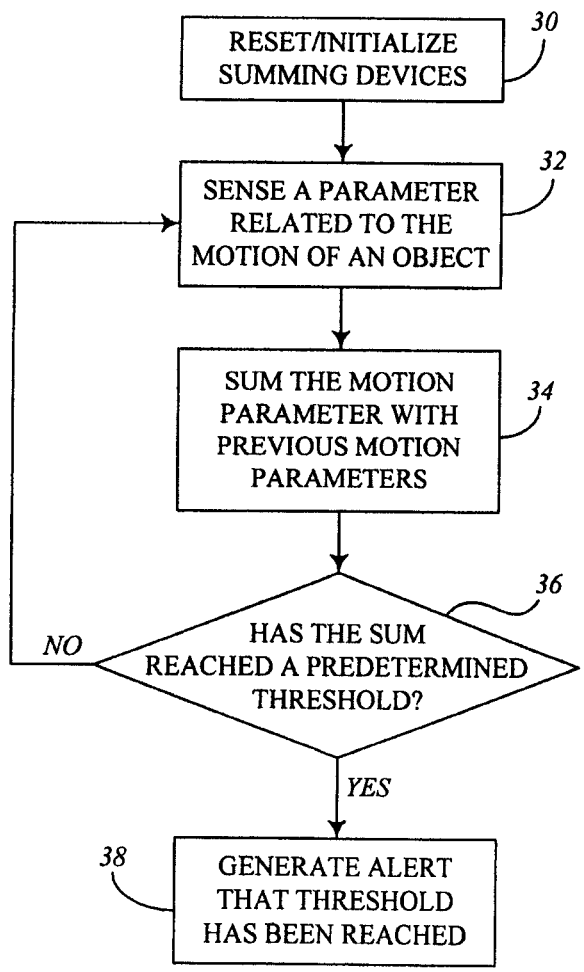
FIG. 3 is a flow chart illustrating a method for monitoring brush strokes according to one embodiment.

FIG. 3 is a flow chart illustrating an embodiment of a method for handling aspects of motion that a user physically exerts on an object. As indicated in block 30, summing devices, which are configured either to count a number of strokes or to sum an accumulative total amount of a particular motion parameter, are reset and/or initialized. As indicated in block 32, a parameter related to the motion of an object is sensed. The sensed motion parameter can be detected by any suitable type of detection device capable of sensing vibration, oscillation, rotation, acceleration, or other parameter related to motion or change of motion. In some embodiments, the sensed motion parameter can be converted to an electrical signal if necessary.

As indicated in block 34, the motion parameter that is sensed in block 32 is summed with previously sensed motion parameters. This summation procedure creates a running total or accumulative amount associated with the motion parameter being sensed. The motion parameter may include a count of the number of strokes that the user exerts on the object. In other embodiments, the motion parameter being sensed may be a stroke force or stroke length, wherein an accumulation of forces or lengths is summed in block 34. In some embodiments, the accumulation may involve the building up of an electrical charge, such as for charging up a capacitor.

As indicated in decision block 36, it is determined whether or not the sum has reached a predetermined threshold. When it is determined that the threshold has not been reached, the method flows back to block 32 to continue sensing additional components of the motion parameter. Eventually, when it is determined in block 36 that the threshold is reached, the method proceeds to block 38, which suggests that an alert is generated to notify the user that the threshold has been reached. In embodiments involving the detection of toothbrush usage, the alert is provided to indicate to the user that the current brushing session has adequately provided sufficient brushing to the user's teeth and that the user may stop brushing.

In some environments, video and/or audio alerts associated with various devices may not be sufficient to bring a sensed condition to the attention or within the perception of a user such devices. Weekday morning bathrooms, especially in households with multiple children or in dormitories, can be hectic environments. Emergency rooms, trauma centers, ambulances, accident scenes, and other emergency environments are often chaotic and highly charged. Physical therapy or other exercise environments can be stressful on one hand and boring on the other. In each of these environments, various forms and magnitudes of audio and visual stimuli from multiple sources may bombard a user in ways that make otherwise simple tasks difficult. Variations of these environments may be adrenalin charged in ways that the user actually blocks or is otherwise unable to perceive or discern certain stimuli. Variations of these environments may be mind-numbing in ways that the user becomes lulled into a "zone." Variations of these environments present situations where the user is visually, aurally, and/or cognitively constrained.

For example, and not by way of limitation, in the morning bathroom environment, a user of a toothbrush may have difficulty appreciating how much time the user has actually spent brushing their teeth. For example, and not by way of limitation, in the emergency environment, a user of a bag-valve-mask may have difficulty counting (or counting at an appropriate rate) between squeezes of the bladder. For example, and not by way of limitation, in an exercise environment, a user of exercise equipment may lose track of time, pace, or number of repetitions. In each of these environments, the user may benefit from a device that provides vibrotactile feedback to the user in response to a sensed condition. For example, and not by way of limitation, in a musical environment, a user of a musical instrument may lose track of time or rhythm, pace, or number of repetitions. In each of these environments, the user may benefit from a device that provides vibrotactile feedback to the user in response to a sensed condition.

Figure 4:
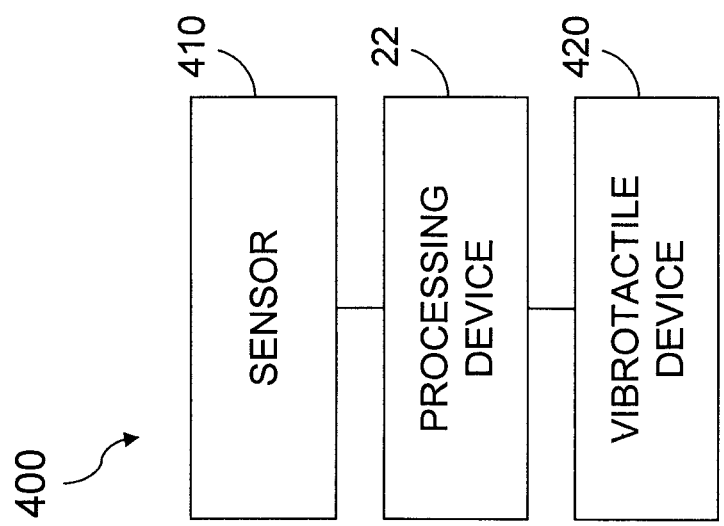
FIG. 4 is a block diagram of a condition sensing system according to various embodiments.

FIG. 4 illustrates a device 400 that may be used in various environments according to various embodiments. Device 400 includes a sensor 410, processing device and a vibrotactile device 420. Sensor 410 senses one or more parameters and provides a sensor output indicative of some aspect of such one or more parameters. Processing device 22 processes the sensor output from sensor 410 and upon an occurrence of one or more conditions associated with the sensor output, provides an output to a vibrotactile device 420. Vibrotactile device 420 provides a haptic output (i.e., a haptic effect) to a user of device 400. According to various embodiments, haptic output may include one or more of eccentric rotating mass actuators or linear resonant arrays and other haptic effects as would be appreciated. In some embodiments, the duration of the haptic output may be adjustable by a user or by processing device 22 based on one or more factors as would be appreciated. In some embodiments, a magnitude of the haptic output may be adjustable by a user or by processing device 22 based on one or more factors as would be appreciated.

In some implementations of device 400, such as, but not limited to, toothbrush 10 described above, sensor 410 senses motion and provides a sensor output to processing device 22 based on the sensed motion. Processing device 22 provides an output to vibrotactile device 420 upon occurrence of a sensed condition, e.g., when the number of the sensed motions exceeds a threshold, an accumulated magnitude of the sensed motions exceeds a threshold, or other sensed condition associated with sensor 410 and/or sensor output. Vibrotactile device 420 responds to the output from processing device 22 by providing a haptic effect (e.g., vibration or pulse) to the user via for example, handle 12 of the toothbrush.

In some implementations of device 400, such as, but not limited to, toothbrush 10, sensor 410 senses motion and provides a sensor output to processing device 22 based on the sensed motion. Processing device 22 may measure a time during which sensor 410 senses motion and provides an output to vibrotactile device 420 when the measured time exceeds a predetermined threshold, e.g., two minutes. Processing device 22 may use a timer external to processing device 22 (not otherwise illustrated) or a timer internal to processing device as would be appreciated. Vibrotactile device 420 responds to the output from processing device 22 by providing a haptic effect (e.g., vibration or pulse) to the user via for example, handle 12 of the toothbrush.

Figure 5:
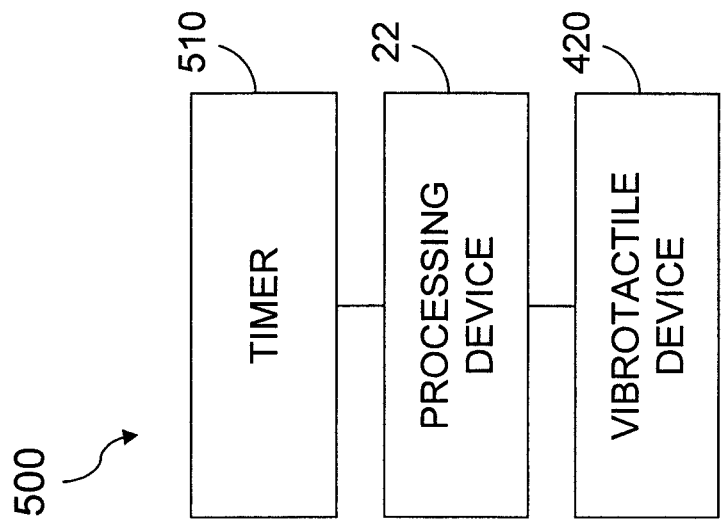
FIG. 5 is a block diagram of a time sensing system according to various embodiments.

FIG. 5 illustrates a device 500 that may be used in various environments according to various embodiments. Device 500 corresponds to an exemplary implementation of device 400 that employs a timer 510. Timer 510 corresponds to particular sensor 410 that senses or otherwise measures time or parameter(s) indicative of time as would be appreciated. Device 500 also includes processing device 22 and vibrotactile device 420. In some embodiments, timer 510 may be external to processing device 22 as would be apparent. In some embodiments, timer 510 may be internal to or otherwise part of processing device 22 as would be apparent. In some embodiments, timer 510 provides a timer output corresponding to at least one time period. In some embodiments, timer 510 provides a timer output corresponding to a plurality of time periods. In some embodiments, timer 510 provides a periodic time period. In some embodiments, timer 510 provides a time period that is adjustable by a user or processing device 22. Processing device 22 measures or otherwise receives timer output and provides an output to vibrotactile device 420 when the measured time exceeds a threshold. In various embodiments, this threshold may be predetermined, adjustable, and/or user selectable as would be appreciated. Vibrotactile device 420 responds to the output from processing device 22 by providing a haptic output (e.g., vibration or pulse) to the user. In various embodiments, the haptic output may be a single haptic output, a plurality of haptic outputs of similar or different durations, a periodic haptic output and/or other haptic outputs.

Figure 6:
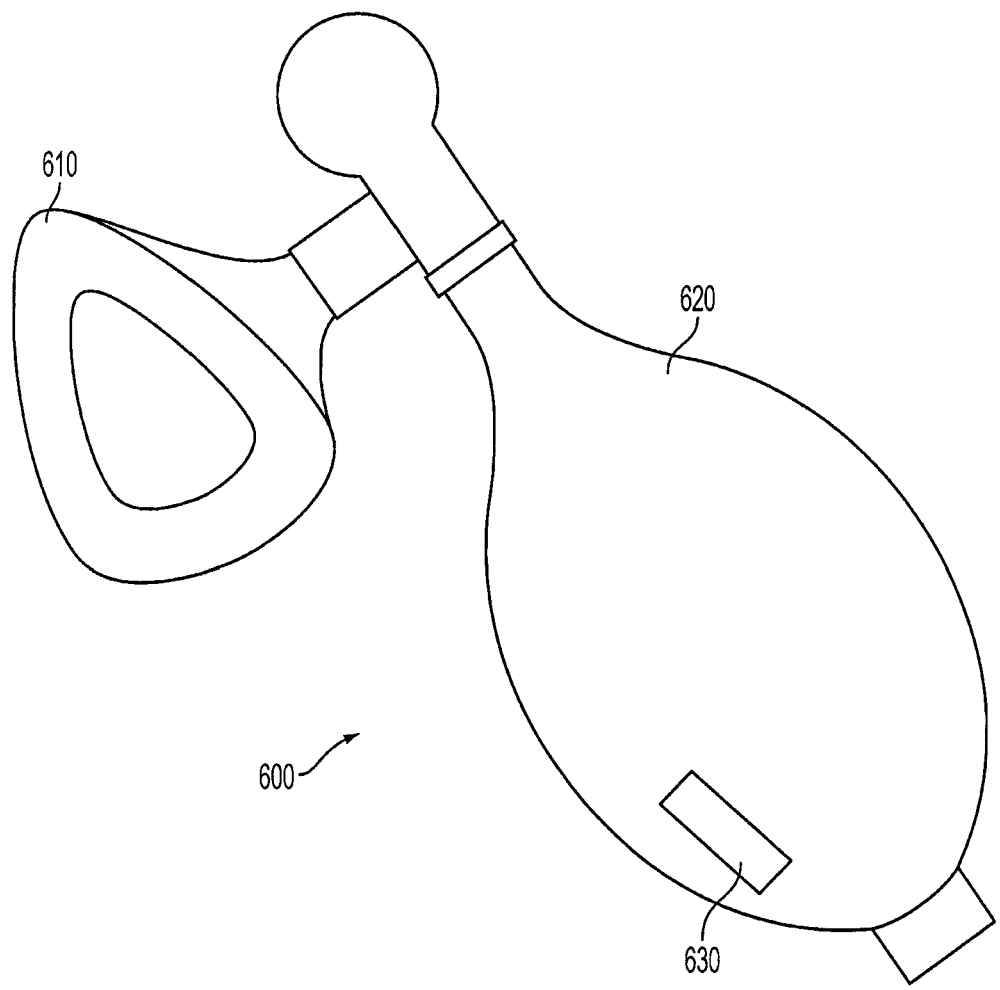
FIG. 6 is an illustration of a bag mask valve having vibrotactile feedback according to various embodiments.

FIG. 6 illustrates an exemplary implementation of various embodiments of device 500, namely, a bag-valve-mask 600 with vibrotactile feedback. Bag-valve-masks may also be referred to as manual ventilators, manual resuscitators, and/or ambu bags. Typically, conventional bag-valve-masks are used by emergency personnel to assist a patient with breathing, for example, during cardiopulmonary resuscitation. Bag-valve-masks include a mask that is placed over the patient's nose and mouth, a bladder, and one or more valves that direct a flow of air from the bladder to the mask when the bladder is squeezed and that draw fresh air and/or oxygen into the bladder when the bladder is released. During resuscitation, the emergency personnel squeezes the bladder at a prescribed rate (squeezes per minute) or with a prescribed period (seconds/counts between squeezes). In emergency environments, the emergency personnel may find maintaining the prescribed rate or the prescribed period difficult due to multiple audio and/or visual stimuli from numerous sources.

Bag-valve-mask 600 may assist emergency personnel with maintaining the prescribed rate or the prescribed period of actuation during resuscitation. Bag-valve-mask 600 includes a mask 610, a bladder 620, and a vibrotactile system 630. Bag-valve-mask 600 includes various valves and may include other conventional features as would be apparent. In some embodiments, vibrotactile system 630 may include timer 510, processing device 22, and vibrotactile device 420. In some embodiments vibrotactile system may also include sensor 410.

In operation, vibrotactile system 630 provides a haptic output to the emergency personnel operating bag-mask-valve 600 at a prescribed rate or with a prescribed period to indicate that the emergency personnel should actuate the bladder. In some embodiments, the haptic output is provided to the emergency personnel via bladder 620. In other words, the emergency personnel perceives or otherwise feels the haptic output through his/her hand(s) holding bladder 620. The emergency personnel may be trained to actuate bladder 620 each time they perceive the haptic output. Bag-valve-mask 600 eliminates a need for the emergency personnel to count between actuations of bladder 620. The haptic output of vibrotactile system 630 operates in conjunction with the emergency personnel on a sensory channel not otherwise overloaded with other stimuli. In some embodiments, bag-valve-mask 600 includes a sensor that detects when bladder 620 has been squeezed. In some embodiments, bag-mask-valve 600 includes a sensor that detects when mask 610 is pressed against a patient's face.

In some embodiments, vibrotactile system 630 provides a haptic output at a haptic output rate or with a haptic output period. In some embodiments, the haptic output rate may be predetermined, adjustable, and/or programmable. In some embodiments, the haptic output rate is selectable by the emergency personnel. In these embodiments, a selectable indicator (not otherwise illustrated) coupled to vibrotactile system 630 may be used to set the haptic output rate, for example, in actuations per minutes. The selectable indicator may include, but is not limited to, a dial, a switch, a pushbutton, or other selectable indicator. In some embodiments, the selectable indicator may include a visual indication of the haptic output rate. As would be appreciated, various embodiments may be based on the haptic output period rather than the haptic output rate.

In some embodiments, a magnitude of the haptic output provided by vibrotactile system 630 may be predetermined, adjustable, and/or programmable. In some embodiments, the magnitude of the haptic output is selectable by the emergency personnel. In these embodiments, a selectable indicator (not otherwise illustrated) coupled to vibrotactile system 630 may be used to set the magnitude of the haptic output. The selectable indicator may include, but is not limited to, a dial, a switch, a pushbutton, or other selectable indicator. In some embodiments, the selectable indicator may include a visual indication of the magnitude of the haptic output.

In some embodiments where vibrotactile system 630 includes sensor 410, vibrotactile system 630 may provide the haptic output based in part on the occurrence of a condition, such as the actuation of bladder 620 sensed by sensor 410. In other words, if vibrotactile system is set to provide a haptic output every 5 seconds, vibrotactile system 630 may provide a haptic output 5 seconds after each time bladder 620 is actuated, rather than every 5 seconds without regard to bladder 620 being actuated. In these embodiments, sensor 410 provides a sensor output each time sensor 410 senses bladder being actuated; timer 510 is reset on receiving the sensor output and provides a timer output once 5 seconds expire; and vibrotactile device 420 provides a haptic output based on the timer output as would be appreciated.

In some embodiments, vibrotactile system 630 may be provided internally to bag mask valve 600. In these embodiments, vibrotactile device may be provided within bladder 620. In some embodiments, vibrotactile system 630 may be provided externally to bag mask valve 600. In some embodiments, some portions of vibrotactile system 630 may be provided externally to bag mask valve 600 and some portions of vibrotactile system 630 may be provided internally to bag mask valve.

Figure 7:
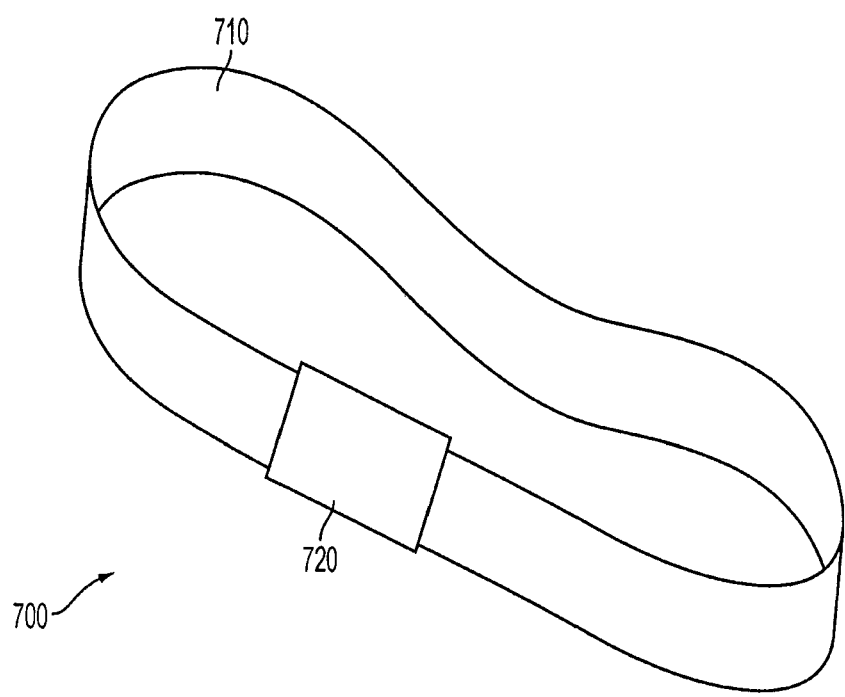
FIG. 7 is an illustration of a physical therapy or exercise system having vibrotactile feedback according to various embodiments.

FIG. 7 illustrates an exemplary implementation of various embodiments of device 400, namely, an exercise strap 700 with vibrotactile feedback. Various exercise regimens require a number of repetitions, a duration for each repetition, a magnitude for each repetition, and/or a pace of each repetition. For example, weight lifters count "reps"; physical therapists specify certain "extensions" and/or "holds" during rehabilitation of a limb or joint; and runners "pace" their strides. All these exercise personnel conduct repetitive tasks that may benefit from receiving stimuli, in the form of a haptic effect, in response to a sensed condition.

Exercise strap 700 may assist exercise personnel with these repetitive tasks during exercise. Exercise strap 700 includes a strap 710 and a vibrotactile system 720. In some embodiments, vibrotactile system 720 includes sensor 410, processing device 22, and vibrotactile device 420. In some embodiments vibrotactile system 720 may also include timer 510.

In operation, vibrotactile system 720 provides a haptic output to the exercise personnel wearing or otherwise utilizing exercise strap 700 upon the occurrence of a sensed condition. In some embodiments, the haptic output is provided to the exercise personnel via vibrotactile system 720 (or more appropriately, vibrotactile device 420) in contact with or otherwise proximate to the exercise personnel so that the exercise feels the haptic output directly from their skin or through their clothing.

The exercise personnel may be conditioned to "exercise" until they perceive the haptic output. In some embodiments, vibrotactile system 720 provides a haptic output on occurrence of a sensed condition. Sensed conditions may include a flexure or extension of a muscle or limb; a number of such flexures or extensions; a rate of such flexures or extensions; a duration of such flexures or extension; a period between such flexures or extensions; and other sensed condition. As described above, sensor 410 operates in conjunction with processing device 22 to identify an occurrence of the sensed condition (e.g., a full extension of a limb) or a number of occurrences of the sensed condition (e.g., ten full extensions of a limb). Processing device 22 provides an output to vibrotactile device 420 which responds by providing a haptic output to the exercise personnel.

In some embodiments, vibrotactile system 720 (and more particularly vibrotactile device 420) of exercise strap 700 provides a haptic output to the exercise personnel when a certain number of repetitions of a sensed condition occurs. In some embodiments, vibrotactile device 420 provides a haptic output to the exercise personnel each time a full "flexure" or "extension" of a limb occurs, for example. In these embodiments, a second haptic output perceptively different from a first haptic output may be provided when a certain number of full "flexures" or "extensions" of the limb occurs.

In some embodiments, vibrotactile system 720 provides a haptic output at a haptic output rate or with a haptic output period. In some embodiments, the haptic output rate may be predetermined, adjustable, and/or programmable. This may be advantageous to runners, cyclists or crew members attempting to achieve a desire pace or consistent stroke.

Again, as discussed above, in some embodiments, the haptic output rate, haptic output period, and/or the magnitude of the haptic output may be selectable by the exercise personnel. In some embodiments, a number of repetitions may be similarly specified by the exercise personnel.

In some embodiments not otherwise illustrated, vibrotactile system 720 may incorporated into or with elements other than strap 710. For example, vibrotactile system 720 may be incorporated into a watch or heart rate monitor as would be appreciated.

It should be understood that the steps, processes, or operations described herein may represent any module or code sequence that can be implemented in software or firmware. In this regard, these modules and code sequences can include commands or instructions for executing specific logical steps, processes, or operations within physical components. It should further be understood that one or more of the steps, processes, and/or operations described herein may be executed substantially simultaneously or in a different order than explicitly described, as would be understood by one of ordinary skill in the art.

The embodiments described herein represent a number of implementation examples and are not intended to necessarily limit the present disclosure to any specific embodiments. Instead, various modifications can be made to these embodiments as would be understood by one of ordinary skill in the art. Any such modifications are intended to be included within the spirit and scope of the present disclosure and protected by the following claims.

What is claimed is:

1. An apparatus comprising:
a motion sensing device supported by an object and configured to sense a plurality of motion parameters related to the movement of the object caused by forces exerted on the object by a user, wherein the motion sensing device comprises a stationary electrical coil and a magnetic rod that is moveable within the electrical coil;
a processing device including a capacitor that is charged by the motion sensing device, the processing device configured to determine when the charge on the capacitor reaches a predetermined threshold; and
an alerting device configured to alert the user when the charge reaches the predetermined threshold.

2. The apparatus of claim 1, wherein the alerting device configured to alert the user when the charge reaches the predetermined threshold comprises a vibrotactile device.

3. The apparatus of claim 2, further comprising:
a strap to which the object is attached such that when the strap is worn on a limb of the user,
the motion sensing device senses motion of the limb, and
the user perceives a haptic output of the vibrotactile device when the charge reaches the predetermined threshold.

4. The apparatus of claim 1, wherein the object is wearable by the user.

\* \* \* \* \*